United States Patent [19]

Mueller et al.

[11] Patent Number: 5,066,679
[45] Date of Patent: Nov. 19, 1991

[54] PHENOLIC THIOALKYLAMIDES AS INHIBITORS OF 5-LIPOXYGENASE

[75] Inventors: Richard A. Mueller, Glencoe; Richard A. Partis, Evanston, both of Ill.

[73] Assignee: G. D. Searle & Co., Chicago, Ill.

[21] Appl. No.: 321,034

[22] Filed: Mar. 9, 1989

Related U.S. Application Data

[63] Continuation of Ser. No. 58,431, Jun. 5, 1987, Pat. No. 4,835,189.

[51] Int. Cl.$^5$ .................... A61K 31/65; C07C 323/22
[52] U.S. Cl. .................................. 514/618; 514/617; 564/161; 564/162
[58] Field of Search ......................... 564/162; 514/618

[56] References Cited

U.S. PATENT DOCUMENTS

| | | | |
|---|---|---|---|
| 4,029,812 | 6/1977 | Wagner et al. | 564/162 |
| 4,327,111 | 4/1982 | Sundeen et al. | 564/162 |
| 4,329,363 | 5/1982 | Dorn et al. | 564/162 |

FOREIGN PATENT DOCUMENTS 1207461 10/1970 United Kingdom ................ 564/162

OTHER PUBLICATIONS

Muller et al., "Hydroxyphenylthio-Substituted Anilides", CA 105, 208614x, Dec. 8, 1986.

*Primary Examiner*—Glennon H. Hollrah
*Attorney, Agent, or Firm*—Mary Jo Kanady; Paul D. Matukaitis

[57] ABSTRACT

The compounds of the present invention comprise substituted phenolic thioalkylamides that are specific inhibitors of 5-lipoxygenase and which, therefore, are useful in the treatment of local and systemic inflammation, allergy and hypersensitivity reactions and other disorders in which agents formed in the 5-lipoxygenase metabolic pathway are involved.

5 Claims, No Drawings

PHENOLIC THIOALKYLAMIDES AS INHIBITORS OF 5-LIPOXYGENASE

This is a continuation of application Ser. No. 07/058,431, filed June 5, 1987 now U.S. Pat. No. 4,835,189.

BACKGROUND OF THE INVENTION

The present invention relates to substituted phenolic thioalkylamides and more particularly relates to the novel compounds of Formula I which are specific 5-lipoxygenase inhibitors and are useful, for example, as anti-inflammatory and anti-allergy agents.

It is well recognized that arachidonic acid, an essential unsaturated fatty acid, is enzymatically oxygenated to various products, including, prostaglandins, thromboxanes, the 5-, 11-, 12- and 15-hydroxyeicosatetraenoic acids (HETEs, DIHETEs) and hydroperoxyeicosatetraenoic acids (HPETEs) and the leukotrienes, all of which have potent physiological effects. The leukotrienes, which are produced via the 5-lipoxygenase Pathway, are the major contributors to the onset of the symptoms of asthma, and mediators for immediate hypersensitivity reactions, inflammation and other allergic responses.

Leukotrienes are found in inflammatory exudates and are involved in the process of cellular invasion during inflammation. The term "leukotrienes" is used as a generic term to describe a class of substances, such as slow-reacting substance (SRS) which is an important mediator in asthma and other hypersensitivity reactions. Immunologically generated SRS is usually referred to as slow-reacting substance of anaphylaxis (SRS-A). SRS-A consists of leukotrienes (LT) known as $A_4$, $B_4$, $C_4$, $D_4$, and $E_4$ $LTC_4$ is at least 100 times more potent than histamine in causing long lasting bronchoconstricting effects The leukotrienes also increase vascular permeability and cause decreased cardiac output and impaired ventricular contraction. $LTB_4$ may be an important mediator of inflammation in, for example, inflammatory bowel disease.

Chemotaxis is a reaction by which the direction of migration of cells is determined by substances in their environment. It is one of the major processes bringing leukocytes from the blood to an inflammatory site, whether the inflammation is caused by an infectious agent, allergic challenge, or other pro-inflammatory stimuli. $LTB_4$ is not only chemotactic for neutrophils and monocytes, but is also highly active in stimulating eosinophil locomotion and possibly that of tumor cells (metastasis). $LTB_4$ also stimulates calcium influx and aggregation of polymorphonuclear leukocytes and $LTB_4$ may, thus, play an important role in mediating both acute and chronic inflammation.

Rheumatoid spondylitis is characterized by an acute neutrophil flareup in the joint which is associated with elevated levels of $LTB_4$. $LTB_4$ is also present in gouty effusions; and exposure to urate crystals is known to stimulate $LTB_4$ production by neutrophils. Accordingly, the 5-lipoxygenase inhibitors of the present invention through inhibition of neutrophil attraction and activation in arthritic joints should reduce the protease and oxidative burden believed responsible for joint destruction in arthritic diseases. Examples of such proteases include elastase, cathepsin G, collagenase and the like.

Aspirin and the other non-steroidal anti-inflammatory agents (NSAIDs) such as indomethacin, ibuprofen, fenoprofen, and the like, inhibit the synthesis of prostaglandins via the cyclooxygenase pathway of arachidonic acid metabolism. These prostaglandin synthetase inhibitors generally exhibit anti-inflammatory, antipyretic and analgesic activity, and are widely used in the treatment of arthritis. The non-steroidal anti-inflammatory agents can lead to the formation of additional pro-inflammatory derivatives of arachidonic acid produced through the 5-lipoxygenase pathway which play a role in immediate hypersensitivity reactions and also have pronounced inflammatory effects Administration of the NSAIDs alone can produce allergic reactions including bronchospastic reactivity; skin rashes; syndrome of abdominal pain, fever, chills, nausea and vomiting; and anaphylaxis. For this reason, aspirin and the other non-steroidal anti-inflammatory agents (NSAIDs) are generally contraindicated for patients suffering from asthma or who have previously exhibited allergic sensitivity to aspirin or other NSAIDs. Co-administration of the 5-lipoxygenase inhibitors of this invention with protease inhibitors and/or cyclooxygenase inhibitors may mitigate the untoward side effects of the latter and allow the increased advantageous use of such cyclooxygenase inhibitors.

Prior to the recognition of the significance of the 5-lipoxygenase pathway of arachidonic acid metabolism in allergic reactions and inflammation, the search for effective therapeutic agents was based primarily on those agents which treated the symptoms of allergy and inflammation. There has since been effort to develop new drugs which selectively block the formation of the mediators of these conditions, and the present invention provides new chemical entities which are inhibitors of the 5-lipoxygenase pathway and are useful in the treatment of asthma, rheumatoid arthritis, psoriasis, inflammatory bowel disease, nephritis, vasculitis, adult respiratory distress syndrome (ARDS) and other allergic, hypersensitivity, and inflammatory conditions.

See Bengt Samuelsson, "Leukotrienes: Mediators of Immediate Hypersensitivity Reactions and Inflammation", *Science*, 220, 568–575 (1983); Michael K. Bach, "Inhibitors of Leukotriene Synthesis and Action", *The Leukotrienes, Chemistry and Biology*, pp 163–194 (Academic Press, Inc., 1984); C. W. Lee et al., "Human Biology and Immunoreactivity of Leukotrienes", *Advances in Inflammation Research*, Volume 6, pp 219–225 (Raven Press, New York 1984); Editorial, "Leukotrienes and other Lipoxygenase Products in the Pathogenesis and Therapy of Psoriasis and Dermatoses", *Arch. Dermatol*, 119, 541–547 (1983); Robert A. Lewis et al., "A Review of Recent Contributions on Biologically active Products of Arachidonate Conversion", *Int. J. Immunopharmac.*, 4, 85–90 (1982); Michael K. Bach, *Biochemical Pharmacology*, 23, 515–521 (1984); and E. L. Becker, *Chemotactic Factors of Inflammation*, pp 223–225 (Elsevier Science Publishers V. B., Amsterdam, 1983); P. Sharon, and W. F. Stenson, *Gastroenterology*, 84, 454 (1984); and M. W. Musch, et al., *Science*, 217, 1255 (1982).

The present invention provides compounds which block the 5-lipoxygenase metabolic pathway and, therefore, block the formation of the leukotrienes responsible for allergy and inflammation, and represent therapeutic agents which are useful in the treatment of allergic and hypersensitivity reactions and inflammation, alone, or also may be utilized in combination with other lipoxygenase inhibitors or with cyclooxygenase inhibitors such as the non-steroidal anti-inflammatory agents.

U.S. Pat. Nos. 4,029,812, 4,076,841 and 4,078,084 disclose compounds of the formula

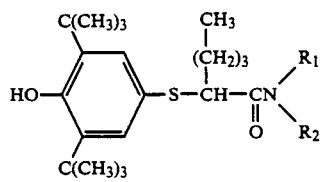

comprising 2-(3,5-di-tert-butyl-4-hydroxy-phenyl)thio carboxamides. The compounds are indicated to be useful in lowering serum lipid levels, in particular serum cholesterol and triglyceride levels. There is no disclosure of any 5-lipoxygenase inhibition activity for these compounds A series of thioethers, useful as, for example, polyfunctional antioxidants for polymers, and biologically active substances, obtained by the nucleophilic addition of thiols, including 3,5-di-tert-butyl-4-hydroxythiophenol, and hydrogen sulfide to acrylate derivatives have been described. See Medvedev et al., *Izv Vyssh. Uchebn Zaved., Khim. Khim Tekhnol.*, 20, 568–574 (1977). The compounds resulting from the foregoing process have the general formulas $RS(CH_2)_nX$ and $S(CH_2CH_2X)_2$ in which R is 3,5-di-tert-butyl-4-hydroxyphenyl and X represents, for example, —C≡N, $NH_2$, $CH(OH)CH_2Cl$, OH, COCl, and various carboxy, carboxylate and amide functions. Compounds of formula I according to the present invention or 5-lipoxygenase activity for structurally related compounds are not disclosed.

U.S. Pat. No. 4,153,803 discloses cholesterol-lowering phenoxyalkanoic acid esters of the formula

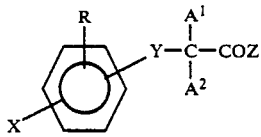

wherein, when Y is sulfur, X is hydrogen, benzyl, benzyloxy, benzylthio, or substituted derivatives thereof; R is hydrogen, halogen, hydroxy, alkyl, or alkoxy; $A^1$ and $A^2$ are hydrogen or alkyl; and Z is amine, azacyclohydrocarbonyloxy, alkoxy of 1–4 carbons, hydroxy, O—M+ where M is a cation, cycloalkoxy of 3–6 ring carbons, tertiaryaminoalkoxy, pivaloyloxyalkoxy, or pyridyl-C-oxy.

European Patent Application 86 101296.1, published Aug. 13, 1986, discloses 5-lipoxygenase inhibiting anilides represented by the formula

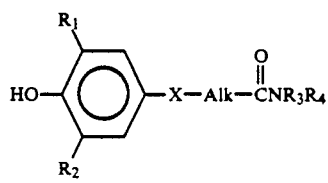

wherein: $R_1$ and $R_2$ are the same or different members of the group consisting of halo, phenyl, substituted phenyl and a

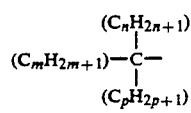

group wherein n, m and p are independently an integer of from 1 to 8 provided that n+m+p is equal to or less than 10; X is thio, sulfinyl or sulfonyl; Alk is straight or branched chain lower alkylene; $R_3$ is hydrogen or lower alkyl; and $R_4$ is phenyl or substituted phenyl.

The compounds are useful in the treatment of allergy hypersensitivity reactions and inflammation, and are particularly useful in the treatment of arthritis and other inflammatory joint disease, asthma, proliferative skin disease such as psoriasis, and the like, alone or in combination with one or more cyclooxygenase inhibitors.

European Patent Application No. 86 101298.7, published Aug. 13, 1986, discloses 5-lipoxygenase inhibiting aminoalkylpyridineamides of the formula

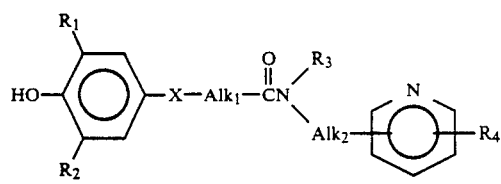

wherein: $R_1$ and $R_2$ are the same or different members of the group consisting of halo, phenyl, substituted phenyl and a

group wherein n, m and p are independently an integer of from 1 to 8 provided n+m+p is equal to or less than 10; X is thio, sulfinyl or sulfonyl; $Alk_1$ is straight or branched chain lower alkylene of 1 to 6 carbon atoms, $R_3$ is lower alkyl, $Alk_2$ is straight or branched chain alkylene of 1 to 4 carbon atoms: $R_4$ is selected from the group consisting of hydrogen, halo, hydroxy, lower alkyl and lower alkoxy; and the pharmaceutically acceptable salts thereof.

The compounds are useful in the treatment of allergy and hypersensitivity reactions and inflammation, and are particularly useful in the treatment of arthritis and other inflammatory joint disease, asthma, proliferative skin disease such as psoriasis, and the like, alone or in combination with one or more cyclooxygenase inhibitors.

European Patent Application No. 86 101299.5, published Aug. 13, 1986, discloses 5-lipoxygenase inhibiting bicycloalkyl, tricycloalkyl, azabicycloalkyl and azatricycloalkyl amides of the formula

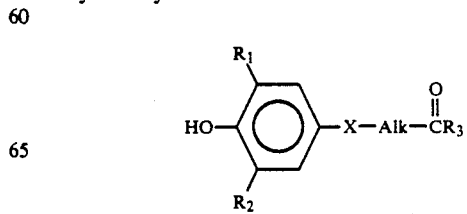

wherein: $R_1$ and $R_2$ are the same or different members of the group consisting of halo, phenyl, substituted phenyl and a

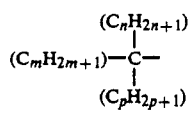

group wherein n, m and p are independently an integer of from 1 to 8 provided that $n+m+p$ is equal to or less than 10; X is thio, sulfinyl or sulfonyl; Alk is straight or branched chain lower alkylene, and $R_3$ is selected from the group consisting of a bicycloalkylamino, tricycloalkylamino, azabicycloalkyl, azatricycloalkyl, azabicycloalkylamino, azatricycloalkylamino or dicycloalkylamino.

The compounds are useful in the treatment of allergy and hypersensitivity reactions and inflammation, and are particularly useful in the treatment of arthritis and other inflammatory joint disease, asthma, proliferative skin disease such as psoriasis, and the like, alone or in combination with one or more cyclooxygenase inhibitors.

SUMMARY OF THE INVENTION

It is, therefore, a primary object of the present invention to provide novel substituted phenolic thioethers.

It is a further object of the present invention to provide methods for promoting anti-allergic and anti-inflammatory effects in mammals in need thereof by the administration of preselected dosages of the compounds of the present invention or pharmaceutically acceptable salts thereof in appropriate non-toxic pharmaceutical dosage forms or compositions.

Another object of the present invention is to provide unit dosage forms adapted for, e.g., oral or parenteral administration. Such dosage forms would be useful in the treatment, management, and mitigation of allergies, inflammation, hypersensitivity reactions, and related disorders and conditions in which physiologically active agents formed in the 5-lipoxygenase metabolic pathway are involved.

DETAILED DESCRIPTION OF THE PREFERRED EMBODIMENTS

These and other similar objects, advantages and features are accomplished according to the compositions and methods of the invention comprised of compounds of the formula

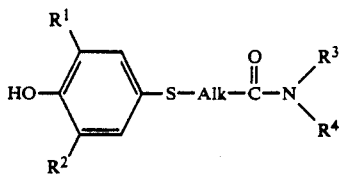

or a pharmaceutically acceptable base addition salt thereof; wherein $R^1$ and $R^2$ are independently $C_4$-$C_{10}$ tert-alkyl; Alk is straight or branched chain lower alkylene;

$R^3$ is:
a) $C_1$-$C_6$ alkyl:
b) phenylalkyl; or
c) benzoylalkyl; and $R^4$ is:
a) hydrogen; or
b) $C_1$-$C_6$ alkyl.

The term "$C_1$-$C_6$ alkyl" refers to straight or branched chain alkyl groups having from 1 to 6 carbon atoms, also referred to as lower alkyl. Examples of $C_1$-$C_6$ alkyl are methyl, ethyl, propyl, butyl, pentyl, hexyl, and the isomeric forms thereof The term Alk, as used herein, refers to straight or branched chain lower alkylene groups having from 1 to 6 carbon atoms, i.e., methylene, ethylene, n-propylene, iso-propylene, n-butylene, sec-butylene, tert-butylene, n-pentylene, 2-methylbutylene, 2,2-dimethylpropylene, n-hexylene and the like.

The term "$C_4$-$C_{10}$ tert-alkyl" as used herein in reference to $R_1$ and $R_2$ refers to branched chain alkyl moieties of from about 4 to 10 carbon atoms having a tertiary carbon atom attached to the phenyl ring substituted by $R^1$ and $R^2$. Examples of such groups are tert-butyl (i.e., 1,1-dimethylethyl), 1,1-dimethylpropyl, 1-methyl-1-(ethyl)pentyl, 1,1-diethylpropyl, 1-ethyl-1-(propyl)butyl, and the like.

The term "phenylalkyl" refers to straight or branched chain $C_1$-$C_6$ alkyl groups substituted with a phenyl group. Examples of phenylalkyl include phenylmethyl, 2-phenylethyl, 3-phenylpropyl, 4-phenylbutyl, 5-phenylpentyl, 6-phenylhexyl, and the isomeric forms thereof.

The term "benzoylalkyl" refers to straight or branched chain $C_1$-$C_6$ alkyl groups substituted with a benzoyl group. Examples of benzoylalkyl include benzoylmethyl, 2-benzoylethyl, 3-benzoylpropyl, 4-benzoylbutyl, 5-benzoylpentyl, 6-benzoylhexyl, and the isomeric forms thereof.

The term "pharmaceutically acceptable base addition salt" refers to a salt prepared by contacting a compound of Formula I with a base whose cation is generally considered suitable for human consumption. Examples of pharmaceutically acceptable addition salts include lithium, sodium, potassium, magnesium, calcium, titanium, ammonium, alkylammonium, dialkylammonium, trialkylammonium, tetraalkylammonium, triethanolamine, lysine, and guanidinium salts.

It will be appreciated by those skilled in the art that when $R^3$, $R^4$ or Alk in Formula I represents branched chain alkyl or m is 1, one or more asymmetric centers may exist and accordingly enantiomers or disastereomers and mixtures may be obtained. The present invention includes such mixtures as well as the separate isomers. The present invention includes any mixtures of enantiomers or diastereomers as well as the separate isomers.

The preferred embodiments of this invention include compounds of the following general structure:

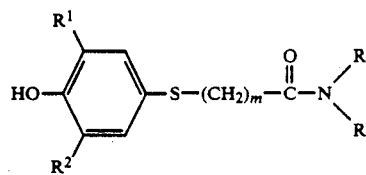

or a pharmaceutically acceptable base addition salt thereof; wherein $R^1$ and $R^2$ are independently $C_4$-$C_{10}$ tert-alkyl;

$R^3$ is:

a) $C_1$-$C_6$ alkyl:
b) phenylalkyl; or
c) benzoylalkyl;
$R^4$ is:
a) hydrogen; or
b) $C_1$-$C_6$ alkyl; and
m is an integer of from 1 to 5.

The most preferred embodiments of this invention include compounds of the following general structure:

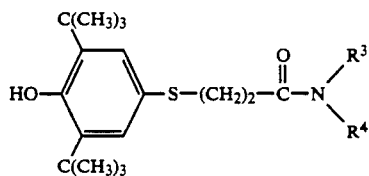

or a pharmaceutically acceptable base addition salt thereof; wherein $R^3$ is $C_1$-$C_6$ or phenylalkyl, and $R^4$ is $C_1$-$C_6$ alkyl.

The compounds of the present invention can be administered in such oral dosage forms as tablets, capsules, pills, powders, granules, elixirs, or syrups as well as aerosols for inhalation. Likewise, administration may be effected intravascularly, subcutaneously, or intramuscularly using dosage forms known to those of ordinary skill in the pharmaceutical arts. In general, the preferred form of administration is oral. An effective but nontoxic amount of the compound is employed in treatment. The dosage regimen utilizing the present compounds is selected in accordance with a variety of factors including the type, age, weight, sex, and medical condition of the patient; the severity of the condition to be ameliorated; and the route of administration. A physician of ordinary skill can readily determine and prescribe the effective amount of the drug required to prevent, treat or arrest the progress of the condition. Dosages of the compounds of the present invention, will range generally between about 0.1 mg/kg/day to about 100 mg/kg/day and preferably between about 0.5 mg/kg/day to about 50 mg/kg/day when administered to patients suffering from allergic or hypersensitivity reactions or inflammation. The compounds may also be administered transdermally or topically to treat proliferative skin conditions such as psoriasis. The daily dosage may be administered in a single dose or in equal divided doses three or four times daily.

In the pharmaceutical compositions and methods of the present invention, at least one of the active compounds of the invention or a pharmaceutically acceptable salt thereof will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug component may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug component may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like.

The compounds of the invention are easily prepared from readily available starting materials by any of the following alternate processes in a conventional manner. The following reaction schemes describe the methods employed for preparing the compounds of formula I, including starting materials, intermediates, and reaction conditions.

The compounds of this invention may be prepared by the methods illustrated in the following Scheme A. Unless otherwise specified, the various substituents are defined as for Formula I, above.

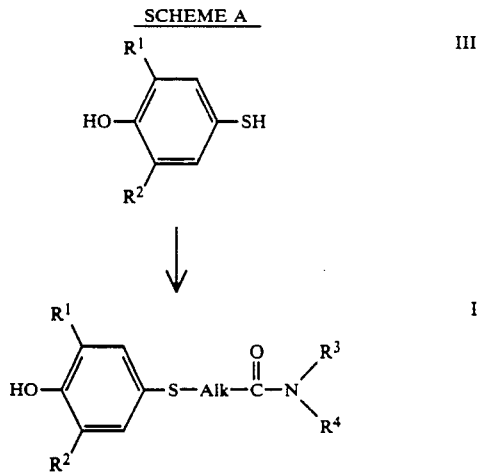

Alkylation of disubstituted 4-mercaptophenols of Formula III with suitable alkylating reagents using methods known to those skilled in the art yields thioalkylamides of Formula I. Alkylation conditions include stirring a compound of Formula III with an alkylating reagent of the formula Halogen-Alk-CO-NR$^3$R$^4$ (where the halogen is preferably bromine or chlorine) in a suitable organic solvent containing a suitable base. For compounds of Formula I in which Alk is (CH$_2$)m and m is 2, a preferred method of alkylation employs acrylamides of the formula CH$_2$=CH—CONR$^3$R$^4$ under similar reaction conditions. Alternatively, halosubstituted esters and acids may be used as alkylating reagents. If so, the acid can be converted to the acid halide then an amine acylated with standard conditions to the amides of this invention. An ester derivative can be caused to undergo amide-ester exchange by treatment with ammonia or a primary or secondary amine, again using well known methods. Hydroxycarboxylic acid amides, when reacted with an acid, for example trifluoroacetic acid, in the presence of the proper 4-mercaptophenol, can give the products of the invention. Suitable organic solvents are organic liquids in which reactants may be dissolved or suspended but which are otherwise chemically inert Examples of suitable organic solvents include lower alcohols, such as methanol, ethanol, or propanol; ketones, such as acetone or methyl ethyl ketone; esters, such as ethyl acetate; ethers and cyclic ethers, such as tetrahydrofuran; N,N-disubstituted amides, such as dimethylformamide; and other solvents known in the art. Preferred organic solvents include methanol and dichloromethane. Suitable bases for the reaction are chemical compounds that are sufficiently basic to prevent the reaction medium from becoming acidic but which do not themselves form significant quantities of byproducts by reaction with other chemical reagents or with reaction products Examples of suitable bases include alkali metal bicarbonates, such as lithium, sodium, or potassium bicarbonate; alkali metal carbonates, such as lithium, sodium, or potassium carbonate; alkaline earth carbonates, such as calcium carbonate or barium carbonate; and tertiary amines, such as triethylamine, tributylamine, N-methylmorpholine, and the like. A preferred base is triethylamine.

The following non-limiting examples further illustrate details for the preparation of the compounds of the present invention. Those skilled in the art will readily understand and appreciate that known variations of the conditions and procedures in the following preparative methods can be utilized. All temperatures are degrees Celcius unless otherwise noted. Melting points were determined on a Thomas-Hoover melting point apparatus and are uncorrected.

EXAMPLE 1

3,5-bis(1,1-dimethylethyl)-4-hydroxyphenyl thiocyanate

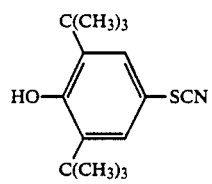

A mixture of 2,6-di-tert-butylphenol (474g, 2.30 mole) and ammonium thiocyanate (76.12g, 4.83 mole) in methanol (1200ml) was stirred with cooling at 0° C. While the temperature was maintained at 0° to 10° C., chlorine gas was slowly bubbled through the mixture for about 1 hour, during which time the reaction mixture became a heterogeneous yellow color. Ammonia was then bubbled through the mixture for about 1.5 hours, during which time the reaction mixture was maintained at a temperature of between 0° to 10° C. The reaction was stirred for an additional hour at 0° C., poured into 2 liters of cold distilled water and refrigerated overnight. The aqueous phase was decanted, and the solid was taken up in methanol, precipitated by addition of water, filtered, and dried for 2 days over phosphorus pentoxide. The resulting gummy yellow solid was recrystallized from pentane and dried in vacuo to yield the product as a white powder, m.p. 61.5°-63° C.

Analysis Calc. for $C_{15}H_{21}NSO$: Theory: C, 68.40; H, 8.03; N, 5.32; S, 12.17 Found: C, 68.85; H,
Found: C, 68.85; H, 8.05; N, 5.29; S, 12.12.

EXAMPLE 2

2,6-bis(1,1-dimethylethyl)-4-mercaptophenol

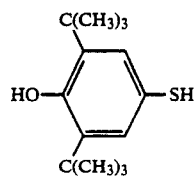

3,5-Bis(1,1-dimethylethyl)-4-hydroxyphenylthiocyanate (55 g, 0.209 mole) was dissolved in acetone (200 ml) under an argon atmosphere. Water (7.6 g, 0.42 mole) was added and the reaction cooled to 0° C. Triethylphosphine (24.7 g, 0.209 mole) was added dropwise over a period of 1 hour and the reaction was then allowed to warm to room temperature with stirring. The solution was concentrated, solvents removed, and the resulting oil purified by chromatography on silica. The fractions containing the thiol were combined and the solvents removed to yield a white powder. Recrystallization from methanol/water yielded, upon drying, 43.3 g of the title compound. The NMR spectrum confirmed the identity of the product.

EXAMPLE 3

3-[[3,5-bis(1,1-dimethylethyl)-4-hydroxyphenyl]thio]-N-(2-oxo-2-phenylethyl)propanamide

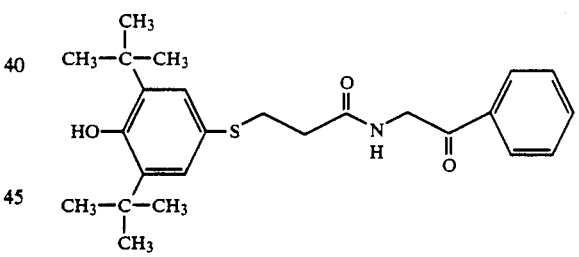

Acryloyl chloride (2 ml) was added to a cold (5°) solution of 2-aminoacetophenone hydrochloride (4.6 g, 27 mmole) and triethylamine (7 ml) in dichloromethane (25 ml) and the mixture was stirred at room temperature. An additional 7 ml of triethylamine was added. After one hour, 2,6-bis(1,1-dimethylethyl)-4-mercaptophenol (11 g, 46 mmole) was added and the mixture heated to reflux. The mixture was allowed to cool to room temperature and the reaction mixture was washed sequentially with 10% hydrochloric acid and water, dried over sodium sulfate, filtered, and concentrated in vacuo. Chromatography on silica gel and recrystallization from ethyl acetate gave the title compound, m.p. 146°-148°. Analysis. Calcd. for $C_{25}H_{33}NO_3S$: C, 70.22; H, 7.78; N, 3.28; S, 7.22. Found: C, 69.95; H, 7.93; N, 3.20; S, 7.62.

EXAMPLE 4

3-[[3,5-bis(1,1-dimethylethyl)-4-hydroxylphenyl]thio]-N-(1-methylethyl)-N-(phenylmethyl)propanamide

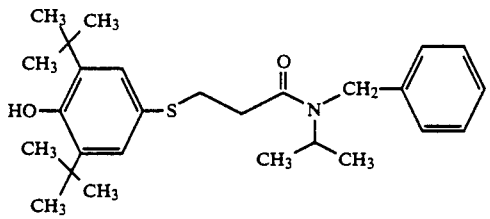

A mixture of 2,6-bis(1,1-dimethylethyl)-4-mercaptophenol (1.19 g, 5 mmole), N-benzyl-N-isopropyl-2-propenamide (1.0 g, 5 mmole) (prepared from acryloyl chloride and benzylisopropylamine), and triethylamine (0.05 ml) in methanol was stirred for 60 hours at room temperature. The reaction mixture was concentrated in vacuo to an oil. Chromatography on silica gel gave the title compound.

Analysis. Calcd. for $C_{27}H_{39}NO_2S$: C, 73.43; H, 8.90; N, 3.17; S, 7.26 Found: C, 73.31; H, 8.87; N, 3.11; S, 7.43.

EXAMPLE 5

3-[[3,5-bis(1,1-dimethylethyl)-4-hydroxyphenyl]thio]-N,N-bis(1-methylethyl)propanamide

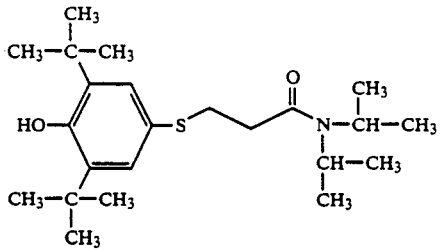

A mixture of 2,6-bis(1,1-dimethylethy)-4-mercaptophenol (2.38 g, 0.01 mole), N,N-diisopropyl-2-propenamide (1.56 g, 0.01 mole) (prepared from acryloyl chloride and diisopropylamine), and triethylamine (0.05 ml) in methanol (25 ml) was stirred for 48 hours at room temperature and then 20 hours at reflux. The reaction mixture was concentrated in vacuo to an oil. Chromatography on silica gel and recrystallization from ethyl acetate-hexane gave the title compound, m.p. 97°-98°. Analysis. Calcd. for $C_{23}H_{39}NO_2S$: C, 70.18; H, 9.99; N, 3.56; S, 8.14 Found: C, 70.42; H, 10.17; N, 3.19; Sm, 8.14.

EXAMPLE 6

2-[[3,5-bis(1,1-dimethylethyl)-4-hydroxyphenyl]thio]-N-(2-oxo-2-phenylethyl) propanamide

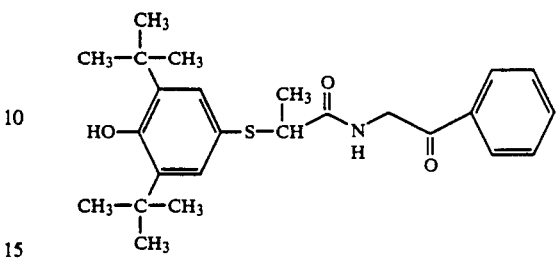

2-Bromopropionyl chloride (5 mmole) is added to a cold (5° C.) solution of 2-aminoacetophenone hydrochloride (5 mmole) in methylene chloride followed by 14 ml of triethylamine in methylene chloride. The mixture is stirred at room temperature. After about 1 hour, the product of Example 2 is added and the solution heated to reflux. The mixture is allowed to cool to room temperature. The reaction mixture is treated as in Example 3 to produce 2-[[3,5-bis(1,1-dimethylethyl)-4-hydroxyphenyl]thio]-N-(2-oxo-2-phenylethyl)propanamide.

BIOLOGICAL EVALUATION

The compounds of the invention are evaluated with respect to 5-lipoxygenase inhibition according to the following assay procedure.

Inhibition of 5-lipoxygenase, in vitro:
anti-inflammatory, anti-allergy activities.

The 100,000×g supernatant fraction of Rat Basophilic Leukemia Cell Homogenate (RBL-1) serves as a 5-lipoxygenase enzyme source. The enzyme is incubated with [1-$^{14}$C)-arachidonic acid and Ca++in the presence and absence of test compound. The product of 5-lipoxygenase, 5-hydroxyeicosatetraenoic acid (5-HETE), is separated by thin-layer chromatography and measured by radioactivity. A compound inhibiting 5-HETE synthesis by 30% or more is considered active at that concentration. Initial screening doses are $1\times10^{-4}$M. When the compound inhibits more than 50% of 5-HETE synthesis at $10^{-4}$M, that compound is tested at multiple dose levels to determine the IC$_{50}$ value (inhibitory concentration to inhibit 50%).

The results with respect to certain of the preferred compounds of the present invention are set forth in Table I.

TABLE I

| Compound Example No. | 5-Lipoxygenase Inhibition, in vitro, IC$_{50}$(μM) |
| --- | --- |
| 4 | 0.56 |
| 5 | 1.40 |

It is further noted that the compounds of the present invention have not been found to be inhibitors of either 12- or 15-lipoxygenases or of cyclooxygenase at concentrations which inhibit 5-lypoxygenase further confirming the specificity of the present compounds for 5-lipoxygenase.

While the invention has been described and illustrated with reference to certain preferred embodiments thereof, those skilled in the art will appreciate that various changes, modifications, and substitutions can be made therein without departing from the spirit of the invention. For example, effective dosages other than the preferred ranges set forth hereinabove may be applicable as a consequence of variations in the responsiveness of the mammal treated, severity of condition treated, dosage related adverse effects, if any, observed and analogous considerations. Likewise, the specific pharmacological responses observed may vary depending upon the particular active compounds selected or whether different active compounds are used in combination or in the presence of suitable pharmaceutical carriers, as well as the type of formulation and mode of administration employed, and such expected variations or differences in results are contemplated in accordance with the objects and practices of the present invention. It is intended, therefore, that the invention be limited only by the scope of the claims which follow.

What is claimed is:

1. A compound of the formula

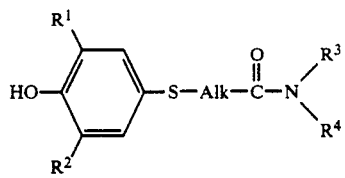

or a pharmaceutically acceptable base addition salt thereof; wherein $R^1$ and $R^2$ are independently $C_4-C_{10}$ tert-alkyl; Alk is ethylene;

$R^3$ is
 a) benzoylalkyl or
 b) phenylalkyl; and
$R^4$ is:
 a) hydrogen or
 b) $C_1-C_6$ alkyl.

2. A compound according to claim 1 which is 3-[[3,5-bis-(1,1-dimethylethyl)-4-hydroxyphenyl]thio]-N-(1-methylethyl)-N-(phenylmethyl)propanamide.

3. A compound according to claim 1 which is 3-[[3,5-bis-(1,1-dimethylethyl)-4-hydroyphenyl]thio]-N-(2oxo-2-phenylethyl)propanamide.

4. A pharmaceutical composition useful in the treatment of lipoxygenase mediated conditions in mammals comprising a pharmaceutically effective amount of a compound of the formula:

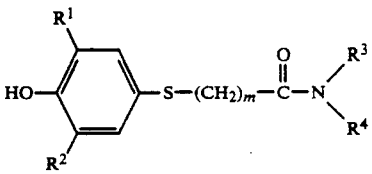

or a pharmaceutically acceptable base addition salt thereof; wherein $R^1$ and $R^2$ are independently $C_4-C_{10}$ tert-alkyl;

$R^3$ is:
 a) benzoylalkyl or
 b) phenylalkyl;
$R^4$ is:
 a) hydrogen; or
 b) $C_1-C_6$ alkyl; and
m is 2 in combination with a pharmaceutically acceptable carrier or diluent.

5. A pharmaceutical composition according to claim 4 wherein said compound is selected from the group consisting of: 3-[[3,5-bis(1,1-dimethylethyl)-4-hydroxyphenyl]thio]-N-(1-methylethyl)-N-(phenylmethyl)-propanamide, and 3-[[3,5-bis(1,1-dimethylethyl)-4-hydroxyphenyl]thio]-N-(2-oxo-2-phenylethyl)propanamide.

* * * * *